United States Patent
Collazo

(10) Patent No.: US 9,402,636 B2
(45) Date of Patent: Aug. 2, 2016

(54) CUTTING GUIDE WITH INTERNAL DISTRACTION

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 50 days.

(21) Appl. No.: 14/563,338

(22) Filed: Dec. 8, 2014

(65) Prior Publication Data

US 2015/0157334 A1     Jun. 11, 2015

Related U.S. Application Data

(63) Continuation of application No. 11/788,377, filed on Apr. 19, 2007, now Pat. No. 8,926,618.

(51) Int. Cl.
| | |
|---|---|
| *A61B 17/15* | (2006.01) |
| *A61B 17/17* | (2006.01) |
| *A61B 17/80* | (2006.01) |
| *A61B 17/56* | (2006.01) |

(52) U.S. Cl.
CPC ............ *A61B 17/152* (2013.01); *A61B 17/1764* (2013.01); *A61B 17/8095* (2013.01); *A61B 2017/565* (2013.01)

(58) Field of Classification Search
CPC ........... A61B 17/1764; A61B 17/8095; A61B 17/152
See application file for complete search history.

(56) References Cited

U.S. PATENT DOCUMENTS

| | | | |
|---|---|---|---|
| 683,184 | A | 9/1901 | Rockwell |
| 1,661,365 | A | 3/1928 | Gendron |
| 1,889,475 | A | 11/1932 | Henkel |
| 3,909,889 | A | 10/1975 | Emerson |
| 3,977,289 | A | 8/1976 | Tuke |
| 4,409,973 | A | 10/1983 | Neufeld |
| 4,421,112 | A | 12/1983 | Mains et al. |
| 4,456,006 | A | 6/1984 | Wevers et al. |
| 4,483,220 | A | 11/1984 | Shindelar |
| 4,509,511 | A | 4/1985 | Neufeld |
| 4,565,191 | A | 1/1986 | Slocum |

(Continued)

OTHER PUBLICATIONS

Outerbridge et al., Stryker Howmedica Osteonics Surgical Techniques, High Tibial Osteotomy Using FirstStep Implants and Instruments, 2001.

(Continued)

*Primary Examiner* — Christian Sevilla
(74) *Attorney, Agent, or Firm* — Lerner, David, Littenberg, Krumholz & Mentlik, LLP

(57) ABSTRACT

A cutting guide for performing a bone osteotomy procedure is disclosed. The cutting guide includes a first arm having a first cutting guide surface formed therein, a second arm having a second cutting guide surface formed therein pivotably connected to the first arm and a distractor operatively connected to the first arm. The cutting guide is adapted to be affixed to the bone such that the first cutting guide surface is open to the second cutting guide surface. The first arm and second arm are rotatable with respect to each other such that manipulation of the distractor creates a force between the first arm and the second arm causing rotation of the first arm and second arm relative to each other. A method for using the cutting guide in a bone osteotomy procedure is also disclosed.

21 Claims, 10 Drawing Sheets

(56) References Cited

U.S. PATENT DOCUMENTS

| | | |
|---|---|---|
| 4,608,898 A | 9/1986 | Volk |
| 4,627,425 A | 12/1986 | Reese |
| 4,632,102 A | 12/1986 | Comparetto |
| 4,677,973 A | 7/1987 | Slocum |
| 4,703,751 A | 11/1987 | Pohl |
| 4,750,481 A | 6/1988 | Reese |
| 4,852,558 A | 8/1989 | Outerbridge |
| 4,913,144 A | 4/1990 | Del Medico et al. |
| 5,041,117 A | 8/1991 | Engelhardt |
| 5,053,039 A | 10/1991 | Hofmann et al. |
| 5,275,603 A | 1/1994 | Ferrante et al. |
| 5,304,180 A | 4/1994 | Slocum |
| 5,413,579 A | 5/1995 | Tom Du Toit |
| 5,540,695 A | 7/1996 | Levy |
| 5,601,565 A | 2/1997 | Huebner |
| 5,613,969 A | 3/1997 | Jenkins, Jr. |
| 5,620,448 A | 4/1997 | Puddu et al. |
| 5,722,978 A | 3/1998 | Jenkins, Jr. |
| 5,749,875 A | 5/1998 | Puddu |
| 5,766,251 A | 6/1998 | Koshino |
| 5,897,559 A | 4/1999 | Masini |
| 5,911,724 A | 6/1999 | Wehrli |
| 5,980,526 A | 11/1999 | Johnson et al. |
| 6,008,433 A | 12/1999 | Stone |
| 6,059,787 A | 5/2000 | Allen |
| 6,086,593 A | 7/2000 | Bonutti |
| 6,203,546 B1 | 3/2001 | MacMahon |
| 6,261,296 B1 | 7/2001 | Aebi et al. |
| 6,348,054 B1 | 2/2002 | Allen |
| 6,423,061 B1 | 7/2002 | Bryant |
| 6,544,266 B1 | 4/2003 | Roger et al. |
| 6,575,982 B1 | 6/2003 | Bonutti |
| 6,755,841 B2 | 6/2004 | Fraser et al. |
| 6,796,986 B2 | 9/2004 | Duffner |
| 6,823,871 B2 | 11/2004 | Schmieding |
| 7,083,624 B2 | 8/2006 | Irving |
| 7,104,996 B2 | 9/2006 | Bonutti |
| 8,192,441 B2 | 6/2012 | Collazo |
| 8,241,292 B2 | 8/2012 | Collazo |
| 8,372,078 B2 | 2/2013 | Collazo |
| 8,545,508 B2 | 10/2013 | Collazo |
| 2002/0164905 A1 | 11/2002 | Bryant |
| 2002/0165552 A1 | 11/2002 | Duffner |
| 2002/0198451 A1 | 12/2002 | Carson |
| 2003/0105526 A1 | 6/2003 | Bryant et al. |
| 2003/0171757 A1 | 9/2003 | Coon et al. |
| 2003/0195516 A1 | 10/2003 | Sterett et al. |
| 2003/0228288 A1 | 12/2003 | Scarborough et al. |
| 2005/0021039 A1 | 1/2005 | Cusick et al. |
| 2005/0075641 A1 | 4/2005 | Singhatat et al. |
| 2005/0154394 A1 | 7/2005 | Michalowicz |
| 2005/0251147 A1 | 11/2005 | Novak |
| 2005/0273112 A1 | 12/2005 | McNamara |
| 2005/0273114 A1 | 12/2005 | Novak |
| 2006/0122617 A1 | 6/2006 | Lavallee et al. |
| 2006/0217808 A1 | 9/2006 | Novak et al. |
| 2006/0241636 A1 | 10/2006 | Novak et al. |
| 2007/0016209 A1 | 1/2007 | Ammann et al. |
| 2007/0213830 A1 | 9/2007 | Ammann et al. |
| 2007/0244487 A1 | 10/2007 | Ammann et al. |
| 2007/0265634 A1 | 11/2007 | Weinstein |
| 2008/0015603 A1 | 1/2008 | Collazo |
| 2008/0015604 A1 | 1/2008 | Collazo |
| 2008/0015605 A1 | 1/2008 | Collazo |
| 2008/0140081 A1 | 6/2008 | Heavener et al. |
| 2008/0140213 A1 | 6/2008 | Ammann et al. |
| 2008/0147073 A1 | 6/2008 | Ammann et al. |
| 2008/0147074 A1 | 6/2008 | Ammann et al. |
| 2008/0154267 A1 | 6/2008 | Merchant et al. |
| 2008/0167654 A1 | 7/2008 | Novak et al. |
| 2008/0208197 A1 | 8/2008 | Ammann et al. |
| 2008/0208199 A1 | 8/2008 | Ammann et al. |
| 2008/0243257 A1 | 10/2008 | Taber |
| 2009/0018543 A1 | 1/2009 | Ammann et al. |
| 2009/0043308 A1 | 2/2009 | Horacek |
| 2009/0054899 A1 | 2/2009 | Ammann et al. |
| 2009/0076512 A1 | 3/2009 | Ammann et al. |
| 2010/0087824 A1 | 4/2010 | Collazo |
| 2014/0074101 A1 | 3/2014 | Collazo |

OTHER PUBLICATIONS

International Search Report, PCT/US2007/014977 dated May 7, 2008.
CD Newton, Principles and Techniques of Osteotomy, Jan. 1, 1985, IVIS, CH. 40.
Henderson et al., Adolescent tibia vara: alternatives for operative treatment, 1992, JBJS-Am, 74, 342-350.
DK Pal et al., Blount's desease in a patient of Indian lineage—A case report, Apr. 2003, IJO, 37-2.
WB Greene, Infantile tibia vara, 1993, JBJS-Am, 75, 130-143.
Office Action from U.S. Appl. No. 11/478,790, mailed Jun. 10, 2009.

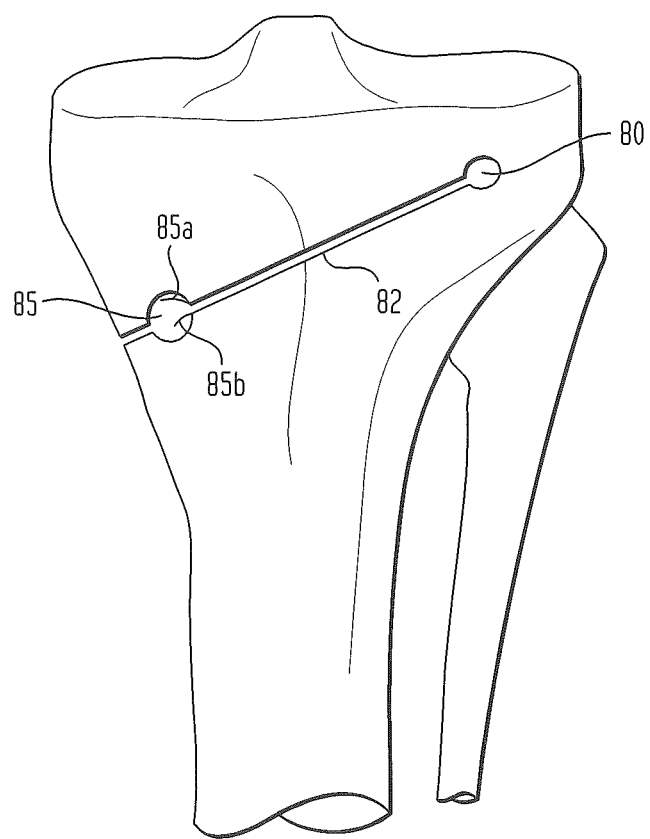

CUTTING GUIDE WITH INTERNAL DISTRACTION

CROSS-REFERENCE TO RELATED APPLICATIONS

The present application is a continuation of U.S. patent application Ser. No. 11/788,377, filed Apr. 19, 2007, the disclosure of which is hereby incorporated herein by reference.

BACKGROUND OF THE INVENTION

High tibial osteotomy ("HTO") procedures have become well-established means of treating unicompartmental degenerative arthritis of the knee. This condition occurs due to uneven weight bearing of the femoral condyles on either of the medial or lateral joint compartments of the tibia. Such uneven weight bearing results from either a varus or valgus defect in the tibia. A varus or valgus defect occurs when the knee joint shifts either medially (valgus) or laterally (varus) with respect to the mechanical axis. It is generally accepted that the preferred location for the mechanical axis of the knee is at about 62% of the tibial plateau from medial to lateral. The process for determining the location of the mechanical axis is known in the art. A varus deformity generally results in increased loading on the medial joint compartment, while a valgus defect results in increased loading on the lateral joint compartment. A high-tibial osteotomy procedure uses one of various techniques to bring the knee into proper mechanical alignment by correcting a deformity therein, whether varus or valgus.

One existing high-tibial osteotomy procedure is the opening wedge HTO. In this procedure, a single cut is made from, for example, the medial cortex of the tibia across to near the lateral cortex in order to correct a varus defect. The cut in an opening wedge HTO procedure extends through almost the entire tibia, leaving only enough bone on the lateral tibia to form a hinge section which serves to keep the tibial plateau connected to the remainder of the bone. The cut is then forced open to form a wedge having an angle corresponding to the required amount of angular correction. This procedure can also be used to correct a valgus defect, with the cut originating on the lateral tibia, extending through the tibia to near the medial tibia. The necessary cut is typically made using a cutting guide, of which various forms are known, affixed to the tibia.

Upon completion of the cut, the cutting guide, should one be used in the procedure, is removed and the bone is typically displaced by inserting two plates into the cut and turning a jackscrew. A metal wedge may also be used to expand the wedge cut by impacting the wedge into the cut and advancing it until the desired amount of correction is achieved. Once the cut is opened, an appropriately shaped spacer can be inserted into the cut to support the tibial plateau at the desired angle. The spacer can be made of a known bone-substitute material, an autograft taken from the patient's iliac crest or an allograft taken from a donor. The wedge is then secured in place using hardware typically in the form of bone plates and screws.

An alternative procedure is what is known as a closing-wedge osteotomy. In such a procedure, a wedge of bone is removed from the tibia, closing the opening left by the removal of the wedge, and securing the bone in its new configuration. The wedge is shaped to correspond to the appropriate amount of angular correction necessary to bring the knee joint into proper alignment. Generally the wedge is shaped so as to span almost the entire medial-lateral width of the tibia, leaving only a narrow "hinge" section of bone on the closed end of the wedge. Once the bone wedge is resected, the opening is forced closed and is typically held in such a position using a staple or other similar device, including bone screws and/or plates. Such procedures are shown in U.S. Pat. No. 5,980,526 to Johnson, et al.; U.S. Pat. No. 6,796,986 to Duffner; U.S. Pat. No. 5,911,724 to Wehrli; U.S. Pat. No. 5,053,039 to Hoffman, et al.; U.S. Pat. No. 5,540,695 to Levy, and; U.S. Pat. No. 5,601,565 to Huebner.

Various tools have been developed in order to facilitate both the opening and closing wedge osteotomy procedures. Typically, these tools include various cutting guides which are capable of being affixed to the bone and provide a surface which is used to guide a bone saw or other known instrument into proper alignment for the desired cut or cuts. Typically, these guides are designed to affix to either the medial or lateral side of the tibia, depending on the type of correction required and the procedure used. By taking either a medial or lateral approach for cutting, the patellar tendon is easily avoided. However, these approaches make alignment of cuts more difficult because the mechanical axis is not visible from the side of the knee. In the use of the various instruments for forming the appropriate cuts for both opening and closing wedge HTO procedures, the instruments must be removed prior to either opening or closing the wedge. This adds an additional step which prolongs the procedure. Furthermore, in the case of opening wedge HTO instrumentation, the device used to open the wedge must often be removed prior to attempting insertion of a filler implant, should one be used. This is problematic, should further opening of the wedge be necessary, as this would require the device to be re-attached to the tibia.

SUMMARY OF THE INVENTION

The present invention relates to a cutting guide for performing a bone osteotomy procedure. The cutting guide includes a first arm having a first cutting guide surface formed therein, a second arm having a second cutting guide surface formed therein pivotably connected to the first arm and a distractor operatively connected to the first arm. The cutting guide is adapted to be affixed to the bone such that the first cutting guide surface is open to the second cutting guide surface. The first arm and second arm are rotatable with respect to each other such that manipulation of the distractor creates a force between the first arm and the second arm causing rotation of the first arm and second arm relative to each other. In a preferred embodiment, the bone is the proximal tibia and the cutting guide is adapted to be affixed to the anterior portion of the proximal tibia.

In a preferred embodiment, the distractor is a screw that is operatively engaged with the first arm by insertion within a threaded hole in the first arm such that rotation of the screw causes axial motion of the screw with respect to the first arm in a direction away from the first cutting guide surface.

In an alternative embodiment, the distractor is a screw, wherein the screw is operatively engaged with the first arm by passing through an opening in the first arm, and wherein the screw is threadibly engaged with a threaded hole in the second arm. The screw may include a head portion with a shoulder section formed therein so as to face an outside surface of the first arm, wherein rotation of the screw causes axial movement of the screw with respect to the second arm such that the shoulder section contacts the outside surface of the first arm.

The cutting guide of the present invention may also include a first rounded groove formed in the first cutting guide surface and a second rounded groove formed in the second cutting guide surface. The first and second rounded grooves together form a drill guide extending from an anterior surface of the cutting guide to a posterior surface of the cutting guide.

In one embodiment of the cutting guide, the hinge portion is disposed on a first side of the patellar tendon and the first and second cutting guide surfaces extend along and contact the proximal tibia on a second side of the patellar tendon. In this embodiment, the first arm may include a first fixation hole and the second arm may include a second fixation hole. The first and second fixation holes are preferably adapted for sliding engagement with respective first and second fixation pins inserted into the second side of the proximal tibia.

In an alternative embodiment of the cutting guide, the first arm and the second arm are connected by a flexible hinge portion extending therebetween such that the cutting guide has an original shape wherein that the first cutting guide surface is substantially parallel to the second cutting guide surface. Preferably, the first arm, the second arm, and the flexible hinge portion are integrally formed. Further preferably, the hinge portion has an inner surface and an outer surface, each of the inner and outer surfaces forming substantially co-axial cylindrical portions. The radius of the outer cylindrical portion is preferably greater than the radius of the inner cylindrical portion by an amount forming a thickness of the hinge portion. The thickness of the hinge portion is preferably sufficient to permit flexing while substantially retaining the original shape of the cutting guide.

A further embodiment of the present invention relates to method of performing a bone osteotomy procedure. The method includes the step of affixing a cutting guide to the bone in a first position. The cutting guide includes a first arm having a first cutting guide surface formed therein, a second arm having a second cutting guide surface formed therein, and a distractor operatively engaged with the first and second arms. The first arm and second arm are rotatable with respect to each other and positioned on the bone such that the first cutting guide surface is open to the second cutting guide surface. The method further includes forming a first cut through a portion of the bone using a cutting instrument in connection with the first and second cutting guide surfaces, and manipulating the distractor so as to cause the first arm to rotate relative to the second arm. Preferably, the bone is the proximal tibia, and the step of affixing the cutting guide to the bone includes affixing the cutting guide to the proximal tibia.

In a further embodiment of the method, the distractor is a screw and is operatively engaged with the first arm by engaging with a threaded hole in the first arm. The step of manipulating the distractor includes rotating the screw so as to cause axial motion of the screw in a direction substantially normal to the first cutting guide surface.

In an alternative embodiment, the distractor is a screw slideably engaged with an opening in the first arm and threadibly engaged with a threaded hole in the second arm. The step of manipulating the distractor includes rotating the screw so as to cause axial motion of the screw relative to the second arm. This method may further include forming a second cut in the proximal tibia at an angle relative to the first cut such that the second cut intersects the first cut so as to create a wedge of bone. The wedge of bone may then be removed from the proximal tibia so as to form a wedge-shaped opening in the proximal tibia. The screw is then rotated so as to cause the first arm and second arm to rotate toward each other so as to close the wedge-shaped opening in the proximal tibia. The second cut may be formed using a cutting instrument in connection with the first and second cutting guide surfaces. The step of forming the second cut may include detaching the cutting guide from the proximal tibia and re-attaching the cutting guide to the proximal tibia in a second position.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

The present invention will be better understood on reading the following detailed description of nonlimiting embodiments thereof, and on examining the accompanying drawings, in which:

FIG. 5 is an anterior elevation view of a proximal tibia having a cut formed therein using the cutting guide shown in FIGS. 1 and 2;

DETAILED DESCRIPTION

Figure 1:
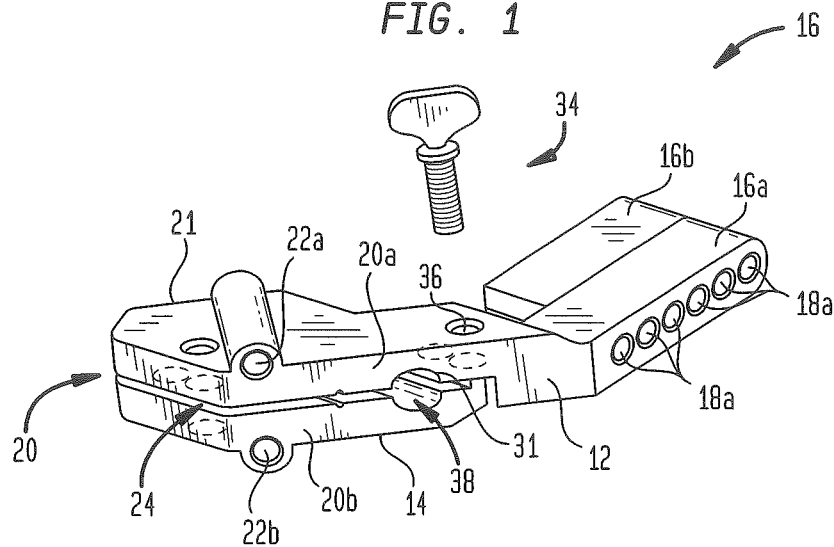
FIG. 1 is an isometric view of a cutting guide according to an embodiment of the present invention.

An exemplary embodiment of a cutting guide 10 according to an embodiment of the present invention is shown in FIG. 1. Generally, cutting guide 10 is adapted to be affixed to a bone surface, and, in the particular embodiment shown in FIG. 1, is adapted to be affixed to the anterior surface of the proximal portion of a human tibia. Cutting guide 10 includes a hinge portion 16 on one end and a guide portion 20 on another end.

Hinge portion 16 is adapted to be positioned partially over the patellar tendon which is associated with the proximal tibia and to extend toward a first side thereof. Guide portion 20 is adapted to contact a portion of the proximal tibia on a second side of the patellar tendon such that hinge portion 16 is spaced apart from the anterior surface of the proximal tibia at a distance adequate to prevent hinge portion 16 from contacting or otherwise interfering with the patellar tendon. By way of example, guide 10 is shown and described as being adapted for performing what is generally-known as an opening wedge HTO including forming a single cut through the medial cortex of a patient's left proximal tibia. As shown in FIGS. 1 through 4, guide portions 20a and 20b are preferably shaped so as to extend from the proximal surface M of the tibia toward and partially contacting the medial surface of the tibia extending substantially toward the posterior cortex of the tibia. Cutting guide slot 24 is preferably included in this portion of cutting guide 10.

In describing preferred embodiments of the cutting block of the present invention, reference will be made to directional nomenclature used in describing the human body. It is noted that this nomenclature is used only for convenience and that it is not intended to be limiting with respect to the scope or structure of the invention. When referring to specific directions, the device is understood to be described only with respect to its orientation and position during an exemplary application to the human body.

Guide 10, preferably, includes two portions: a first arm 12 and a second arm 14. First arm 12 includes a first guide portion 20a and a first hinge portion 16a, and second arm 14 includes a second guide portion 20b and a second hinge portion 16b. Hinge portions 16a, 16b are structured to allow first arm 12 and second arm 14 to rotate with respect to each other. Preferably, this is achieved by including matching holes 18a, 18b in first and second hinge portions 16a, 16b, respectively. In the example of cutting guide 10 shown in FIG. 1, first hinge portion 16a is positioned anteriorily of second hinge portion 16b such that hole 18a aligns with hole 18b along the respective longitudinal axes thereof. A hinge pin or drill bit 50 (not show in FIG. 1) is inserted through holes 18a, 18b to secure the relative position of first and second arms 12, 14 in the proximal-distal and medial-lateral directions while permitting first arm 12 and second arm 14 to rotate relative to each other. Preferably, pin 50 is also used in affixing guide 10 to the proximal tibia by inserting pin 50 into a hole that is formed, preferably by drilling, in the proximal tibia at the appropriate location.

In a preferred embodiment, hinge portions 16a, 16b each include multiple pairs of holes 18a, 18b, which allow the user of guide 10 to select the appropriate pair into which to insert pin 50. This allows guide 10 to be adapted to better fit the shape and structure of the specific proximal tibia on which the procedure is carried out, particularly with respect to the location of guide portion 20 and pin 50.

Guide portion 20 includes a cutting guide slot 24 formed therein, which is adapted for use with various forms of cutting instruments used in orthopedic procedures. These cutting instruments include various forms of bone saws, such as oscillating saws, osteotomes and OTIS saws. Cutting guide slot 24 is formed by a first cutting guide surface 26a formed on first guide portion 20a and a second cutting guide surface 26b formed on second guide portion 20b. First and second arms 12, 14 can be rotated into a position such that first and second cutting guide surfaces 26a, 26b are substantially parallel to each other and are spaced apart from each other at a distance sufficient to accept a cutting instrument therebetween, allowing the cutting instrument to slide freely within cutting guide slot 24 while providing a fit that is sufficient to accurately guide the cutting instrument along a path defined by cutting guide slot 24.

Figure 3:
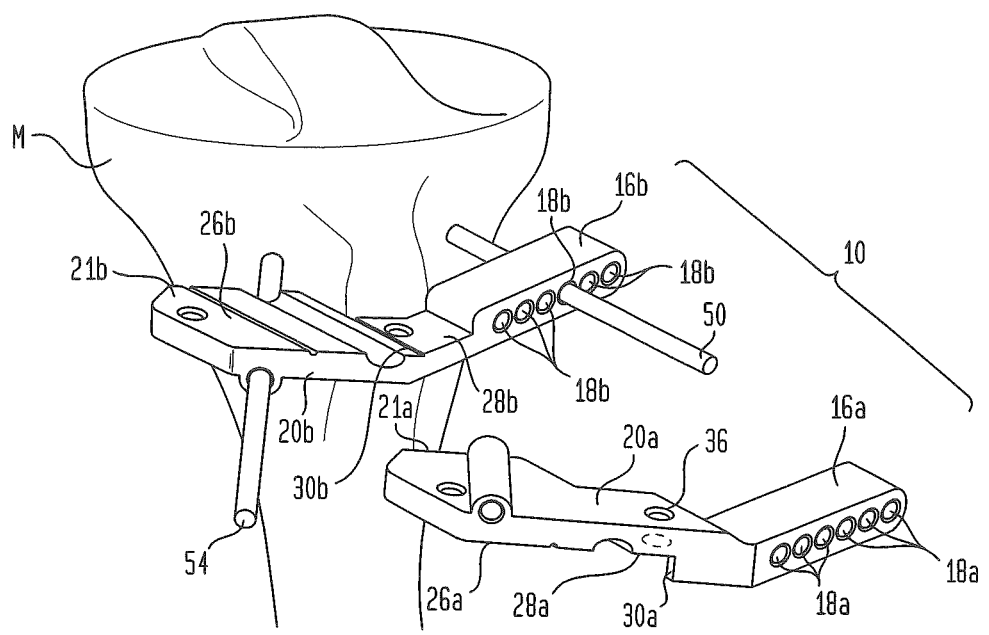
FIG. 3 is an exploded view of the cutting guide shown in FIGS. 1 and 2 affixed to a proximal tibia.
Figure 4:
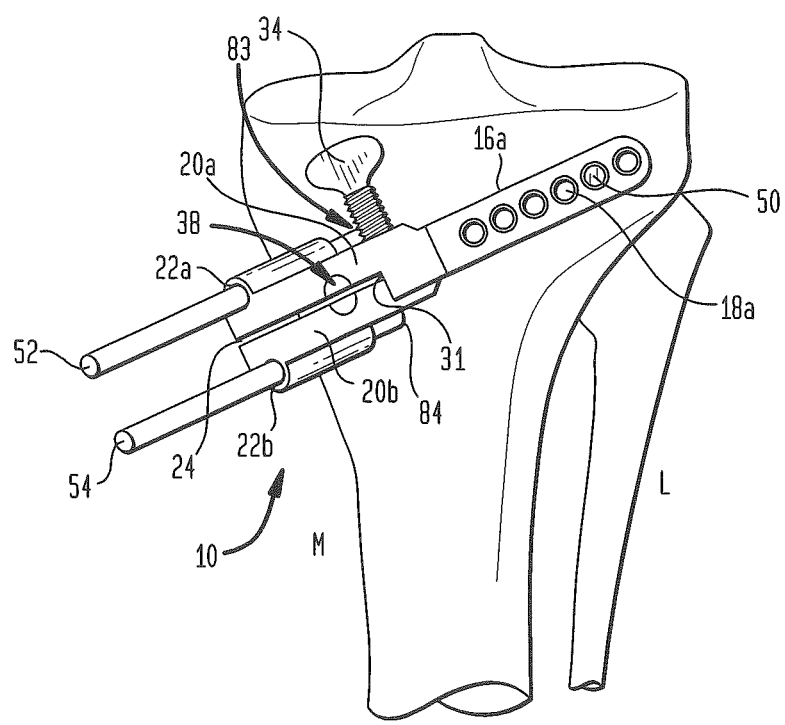
FIG. 4 is an anterior elevation view of the cutting guide shown in FIGS. 1 and 2 affixed to a proximal tibia.

To allow for more accurate spacing between first cutting guide surface 26a and second cutting guide surface 26b during use and placement of cutting guide 10, first arm 12 and second arm 14 can, respectively, include a first blocking surface 28a and a second blocking surface 28b. As shown in FIG. 3, blocking surfaces 28a, 28b are substantially parallel to their respective cutting guide surfaces 26a, 26b and are spaced apart therefrom. Preferably, blocking surfaces 28a, 28b are spaced apart from their respective cutting guide surfaces 26a, 26b at a distance that is approximately equal to half of the desired distance between first and second cutting guide surfaces 26a, 26b. Alternatively, only one blocking surface may be included on either first arm 12 or second arm 14 at a sufficient height to ensure proper spacing between cutting guide surfaces 26a, 26b.

First and second arms 12, 14 can further include vertical walls 30a, 30b, respectively, positioned between the respective cutting guide surfaces 26a, 26b and blocking surfaces 28a, 28b. Vertical walls 30a, 30b act in conjunction with cutting guide surfaces 26a, 26b to form a terminal end 31 for cutting guide slot 24 that can further act to properly guide a cutting instrument during use with cutting guide 10.

Cutting guide 10 further includes a distraction mechanism formed integrally therewith. The distraction mechanism is used in manipulating the rotational relationship between first arm 12 and second arm 14. In the embodiment shown in FIGS. 1-3, the distraction mechanism includes a threaded hole 36 formed in first arm 12 into which a screw 34 is operatively engaged. When screw 34 is advanced into hole 36, it contacts a portion of second arm 14, such as blocking surface 28b, causing a force to be exerted thereon, which acts to cause first arm 12 and second arm 14 to rotate with respect to each other such that first and second cutting guide surfaces 26a, 26b move away from each other. In an alternative embodiment, the distraction mechanism may include a through hole formed in first arm 12, a threaded hole formed in second arm 14 and a screw. The screw passes through the appropriately-sized through hole and engages the treaded hole. The head of the screw is positioned on the outside surface of first arm 12 such that, when screw 34 is advanced into the threaded hole, the inside surface of the screw head is drawn into contact with the first arm. This contact causes a force to be exerted between first and second arms 12, 14 causing rotational movement therebetween such that first and second cutting guide surfaces 26a, 26b move toward one another.

Cutting guide 10 is formed of a material sufficient to give cutting guide 10 an appropriate rigidity to accurately guide a cutting instrument for formation of the cuts necessary for the HTO procedure. Additionally, cutting guide 10 may be made from a material that allows for multiple uses, which includes the ability to be repeatedly subjected to the various sterilization procedures used in the art. Acceptable materials for cutting guide 10 include, but are not limited to, surgical steel, titanium or other similar materials.

Figure 2:
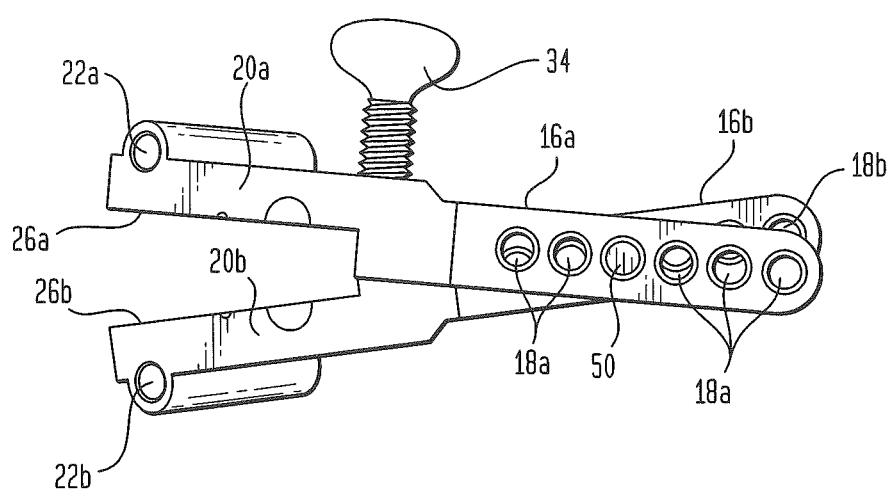
FIG. 2. is an elevation view of the cutting guide of FIG. 1 from an anterior direction.

A further embodiment of the present invention includes a method for performing an opening-wedge high-tibial osteotomy procedure on a patient using guide 10 shown in FIGS. 1-3. In performing this procedure, access is gained to the proximal tibia through an appropriately-sized, retracted incision. First drill hole 80 is formed starting at the anterior portion of the proximal tibia and passing through the posterior cortex thereof. First drill hole 80 should be positioned at the desired apex of the wedge that is to be formed in the surgery. Once first drill hole 80 is formed, the drill bit 50 is removed from the drill and is left in first drill hole 80. Second arm 14 is then assembled onto drill bit 50 by sliding drill bit 50 through hole 18b or an appropriately-selected one of a set of holes. Generally, one of a set of holes 18b is selected such that guide portion 20 contacts the proximal tibia along the back edge 21a thereof, while providing appropriate anterior spacing of hinge portion 16 relative to the patellar tendon, such that hinge portion 16 does not interfere with the patellar tendon. The proper angular alignment is selected for second arm 14, which is such that second cutting guide surface 26b is aligned with the selected position for the cut to be formed in connection with the procedure. Guide hole 22b is then used as a guide for forming second drill hole 84 in the proximal tibia. A first pin 54 is then inserted into second drill hole 84 to secure the position of second arm 14 relative to the proximal tibia.

First arm 12 is then affixed to the proximal tibia by first engaging hole 18a with drill bit 50 and sliding first arm 12 along drill bit 50 until the back edge 21a of first arm 12 contacts the proximal tibia. First arm is then aligned such that first blocking surface 28a contacts second blocking surface 28b. Third drill hole 83 is then formed in the proximal tibia using first hole 22a. A second pin 52 is then inserted through hole 22a and into third drill hole 83. In a preferred embodiment of guide 10, holes 22a are formed substantially parallel to each other and are further formed at an angle relative to holes 18a, 18b such that when pins are inserted into guide 10 so as to affix guide 10 to the proximal tibia, the angular arrangement of pins 52, 54 helps to retain guide in its position.

Once first and second arms 12, 14 of guide 10 are affixed to the proximal tibia in the proper position, a cutting instrument, as described above, is slid into the cutting guide slot 24, which is formed by first and second cutting guide surfaces 26a, 26b, in order to form an appropriate cut 82 in the proximal tibia. Preferably, the cutting instrument is positioned in a generally anterior-posterior direction such that a side edge thereof contacts the terminal end 31 of cutting guide slot 24. Terminal end 31 is preferably of a sufficient length in the anterior-posterior direction to provide stability for the cutting instrument along the plane formed by terminal end 31. Preferably, the cut 82 is initiated by engaging the cutting instrument with cutting guide slot 24 such that an edge of the cutting instrument abuts terminal end 31 so as to be slidably engaged therewith, thereby assisting the user in making cut 82 such that it is oriented substantially in the anterior-posterior direction through the anterior cortex of the tibia without interfering with the patellar tendon. The cutting instrument is then continued to be moved substantially in the anterior-posterior direction until cut 82 penetrates the posterior cortex of the tibia.

Once cut 82 has been started, the user of guide 10 may then proceed to complete cut 82 by freely moving the cutting instrument within cutting guide slot 24. Such movement may include rotating the cutting instrument along the plane formed by cutting guide slot 24 so as to extend cut 82 behind the patellar tendon of the patient and through the entire proximal tibia along the proscribed cutting path. The placement of drill bit 50 at the hinge portion between first and second arms 12, 14 effectively blocks cutting guide therealong, forming the end of the cut at the desired location and providing a widened, rounded apex of the cut that reduces the stress concentration that may result from subsequent expansion of the cut.

Having completed the formation of cut 82 in the proximal tibia, the user of guide 10 then removes the cutting instrument from cutting guide slot 24 and inserts screw 34 into threaded hole 36. Screw 34 is then turned so as to advance it into threaded hole 36 such that the tip of screw 34 contacts a portion of second arm 14 and creates a force between first arm 12 and second arm 14, which is then transferred, via pins 52, 54 into the proximal tibia at a location above and below cut 82. The continued advancement of screw causes cut 82 to open by forcing apart the portions of proximal tibia that are separated by cut 82. This requires the portion of proximal tibia that is left connecting the two separate portions to flex to accommodate the opening cut 82. The screw is turned, thereby opening cut 82 into the shape of a wedge having the appropriate angle for correction of the defect.

Figure 7:
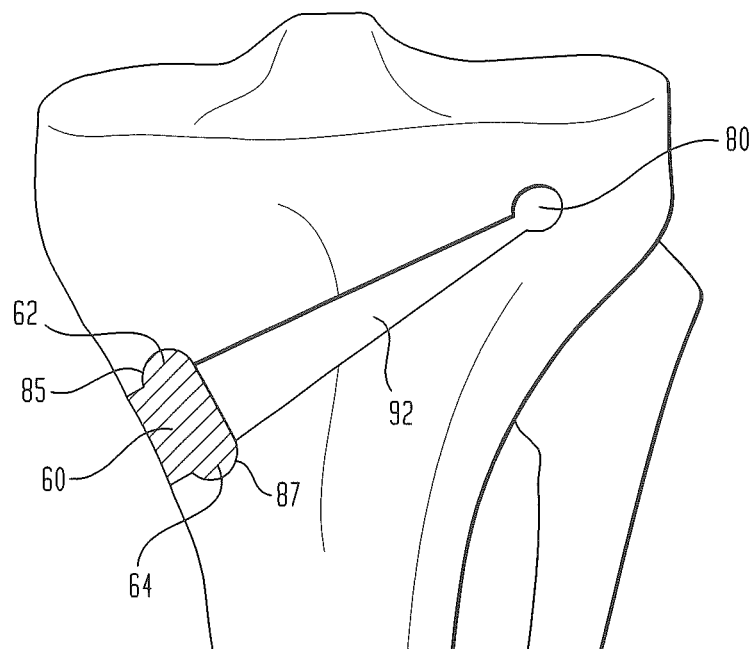
FIG. 7 is an anterior view of a cut formed in a proximal tibia using a cutting block according to an embodiment of the present invention and secured with an implant shown as shown in FIG. 6.
Figure 6:
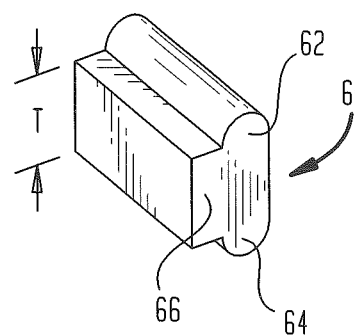
FIG. 6 is an isometric view of an implant used in securing a cut formed during a procedure utilizing the cutting block according to an embodiment of the present invention.
Figure 8:
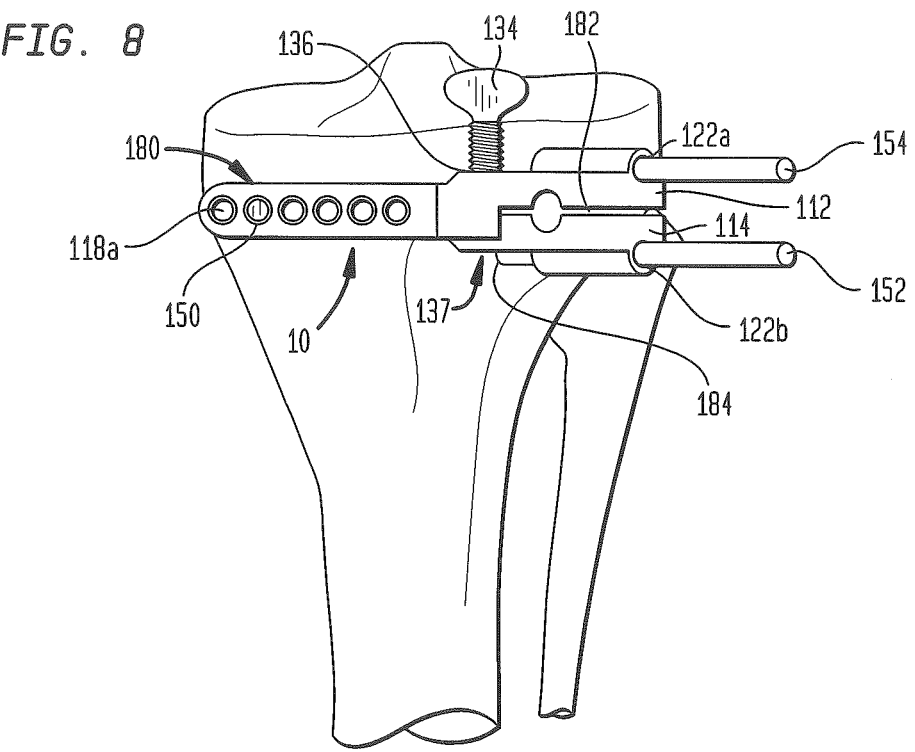
FIGS. 8-11 are anterior views of a proximal tibia having a cutting guide affixed thereto during steps of an HTO procedure.
Figure 9:
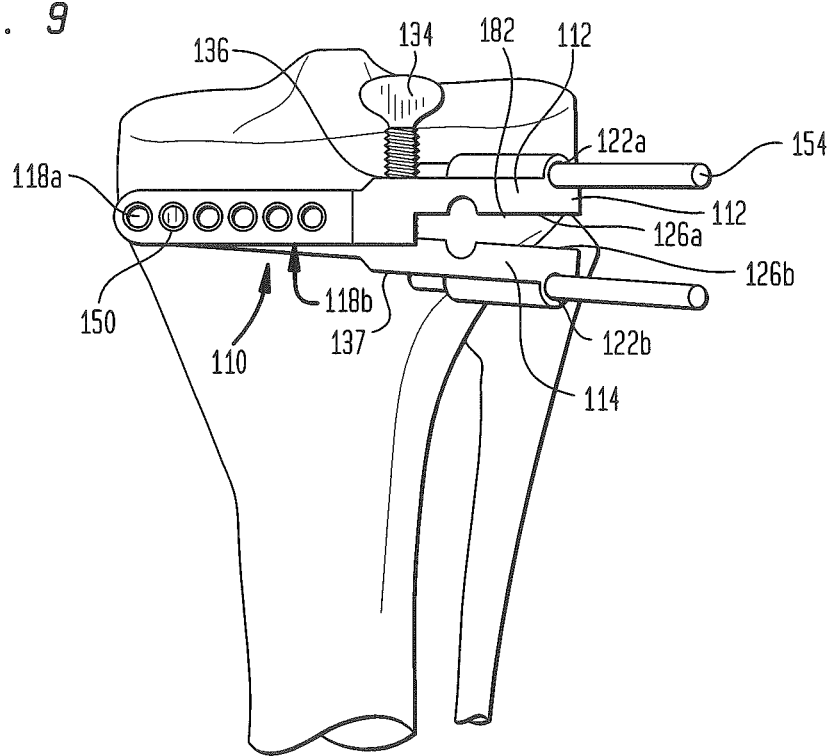
Figure 10:
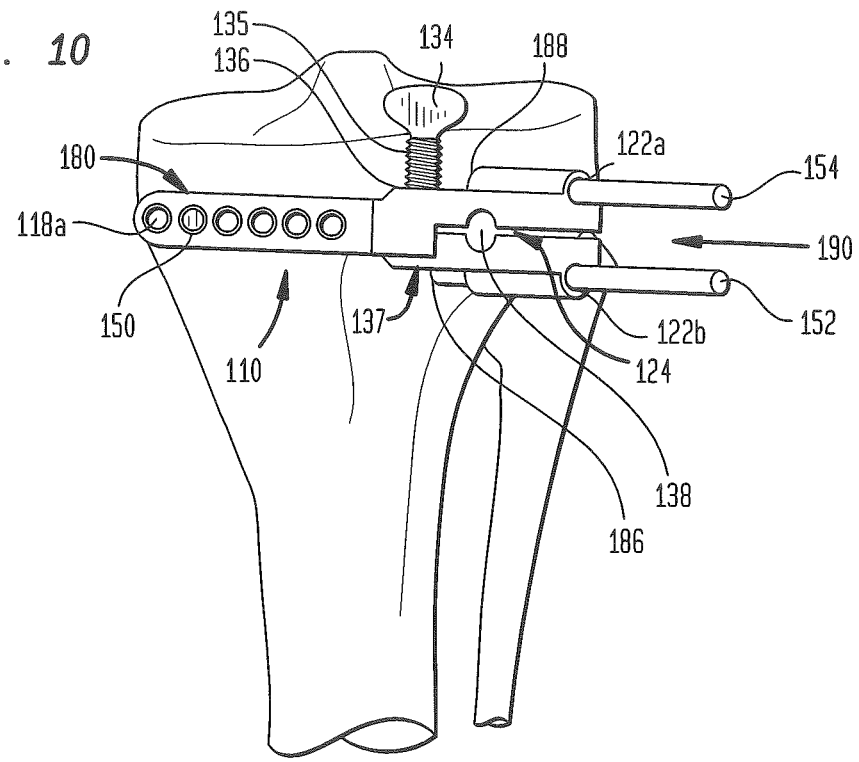
Figure 11:
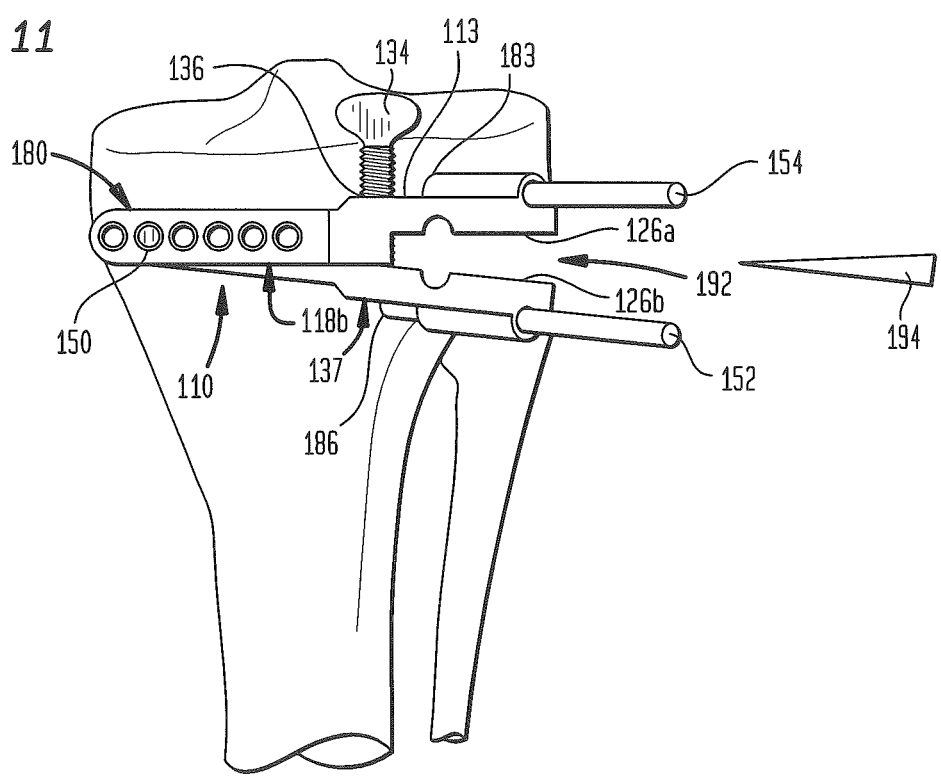

The bone is then secured in the position achieved through advancement of screw. This can be done by using known devices including staples or spacers. A preferred embodiment of guide 10 includes a drill guide 38 formed between first and second cutting guide surfaces 26a, 26b such that a drill can be guided thereby into the proximal tibia when guide 10 is secured to the proximal tibia in the closed position. The drill used in conjunction with drill guide 38 is sized so that portions of the drill hole form semi-cylindrical channels 85a, 85b on both sides of cut 82. In a procedure using such guide, a drill hole is formed using a drill in conjunction with drill guide 38, preferably prior to forming the cut in the proximal tibial. The wedge can then be secured in position using a spacer 60 shown in FIGS. 6 and 7. Spacer 60 includes semi-cylindrical projections 62, 64 extending from opposite sides thereof which are adapted to mate with the corresponding channels 85a, 85b formed in the proximal tibia and a flange 66 that extends between the inner surfaces of the wedge. The thickness T of flange 66 is selected to maintain the appropriate angle for the wedge formed during the procedure. Flange 66 may be angled so as to substantially match the desired angle for the wedge.

The mating of projections 62, 64 with channels 85a, 85b helps to provide stability for the spacer and the joint overall during the healing process. In particular, it helps to add to the torsional stability of the tibial plateau relative to the remainder of the bone to aid in insertion of spacer 60. Screw 34 may be turned so as to expand the size of the wedge beyond the desired angle for correction of the defect. Once spacer 60 is in place, the guide is then removed from the bone, and the wound is closed.

An alternative method for performing an HTO procedure can be completed using a variation of the guide shown in FIGS. 1-5. Guide 110, as shown in FIGS. 8-11 is similar in structure to guide 10, except that screw 134 passes through a through hole 136 in first arm 112 and engages a threaded hole 137 in second arm 114. In this embodiment, screw 134 is used to create a force between first arm and second arm 112, 114 that causes arms 112, 114 to be drawn toward one another. This is accomplished by turning screw 134 such that the bottom edge of the screw head 135 is brought in to contact with the outside surface 113 of first arm 112. The screw is continued to be turned, causing the opposing forces of the screw head on the first arm and the screw threads on the second arm to draw the arms 112, 114 together. Other mechanisms may be used to affect the necessary force between first and second arms 112, 114, including levers, ratchet mechanisms and the like.

The embodiment of guide 110 shown in FIGS. 8-11 is useful in performing a closing wedge HTO procedure, in which two appropriately shaped and located cuts 182, 190 are formed in the proximal tibia in order to form a wedge of bone 194 that is removed from the tibia, thereby creating a wedge-shaped opening 192 therein. The wedge-shaped opening 192 is then drawn closed and secured in order to achieve the desired amount of angular correction for the joint. In performing this procedure, guide 110 is used to form both cuts 182, 190 and to draw the wedge-shaped opening 192 closed.

Guide 110 is used to form first cut 182 by first affixing guide 110 in the appropriate location therefor. This is done by first forming a first hole 180 in the proximal tibia at the desired location for the apex of the wedge 192 that is to be formed. The drill bit 150 used to form the hole 180 may be left in place after formation of hole 180 or may be replaced with a similarly-sized pin. Second arm 114 is then placed on the proximal tibia by engaging an appropriate one of hinge holes 118b with drill bit 150. Second arm 114 is then aligned on the proximal tibia such that second cutting guide surface 126b is aligned with the desired location for the first cut. A second hole 184 is then drilled in the proximal tibia using hole 122b into which first pin 152 is inserted in order to hold second arm 114 in place. First arm 112 is then affixed to the proximal tibia by aligning one of holes 118a that corresponds to the selected one of holes 118b with drill bit 150 and engaging it with hole 118a such that the posterior edge of first arm 112 contacts a portion of the proximal tibia. A third drill hole 183 is then formed in the proximal tibia using hole 122a into which pin 154 is inserted. First cut 182 is then formed using a cutting instrument in connection with cutting guide slot 124 in a manner similar to that which is discussed above.

After formation of first cut 182, pin 152 is removed from the proximal tibia and from hole 122b. Screw 134 is then turned so as to withdraw screw 134 from second arm 114, thereby allowing second arm 114 to rotate away from first arm 112 and causing second cutting guide surface 126b to form an angle relative to first cutting guide surface 126a. Screw 134 is turned until second cutting guide surface 126b is substantially aligned with the desired position for second cut 190. When this alignment is achieved, second arm 114 is, again, secured to the proximal tibia by forming a fourth hole 186 using hole 122b and inserting pin 152 through hole 122b and into fourth hole 186. Pin 154 is then removed from hole 122a in first arm 112 thereby making first arm free to rotate about drill bit 150. First arm 112 is then rotated, either freely or by turning screw 150, such that first blocking surface 28a contacts second blocking surface 28b. First arm is then secured in place by forming fifth drill hole 188 in the proximal tibia and inserting pin 154 through hole 122a and into fifth drill hole 188. Second cut 190 is then formed in the proximal tibia using a cutting instrument in connection with cutting guide slot 124, thereby forming a removable wedge 194 in the proximal tibia.

Pin 154 is then removed from the proximal tibia and from hole 122a. First arm is then rotated such that hole is re-aligned with the second hole 183 formed in the proximal tibia and pin 154 is inserted through hole 22a and into second hole 183. Wedge 194 is then removed from the proximal tibia, forming wedge-shaped opening 192 in the proximal tibia. Opening 192 is then drawn closed using guide 110 by turning screw 134 in the manner described above in order to rotate first and second arms 112, 114 together. The attachment of guide 110 to the proximal tibia will cause opening 192 to close by rotating the tibial plateau with respect to the remainder of the bone. When the wedge is being closed, it may be necessary to remove drill bit 150 from the bone, leaving drill bit 150 engaged with cutting guide 110 or to replace drill bit 150 with a pin of a smaller diameter.

It is to be understood that the particular order of steps described herein is merely exemplary and that the order of the cuts formed may be varied in such a procedure and that the affixation of the various components of guide 110 and the manipulation thereof, as described above, may be altered to accommodate such variations.

Figure 12:
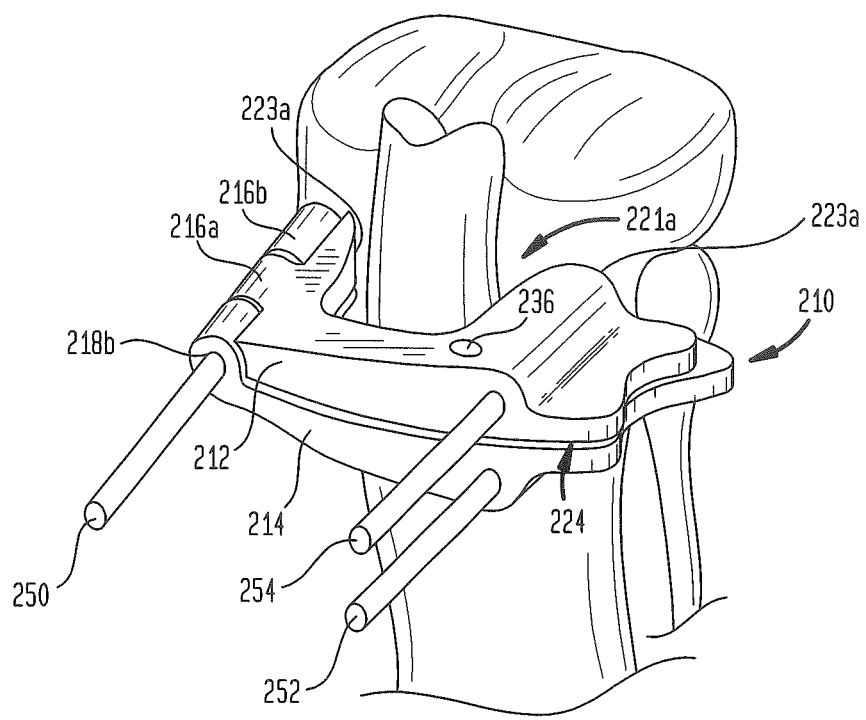
FIG. 12 is an alternative embodiment of a cutting guide for use in a bone osteotomy procedure.
Figure 13:
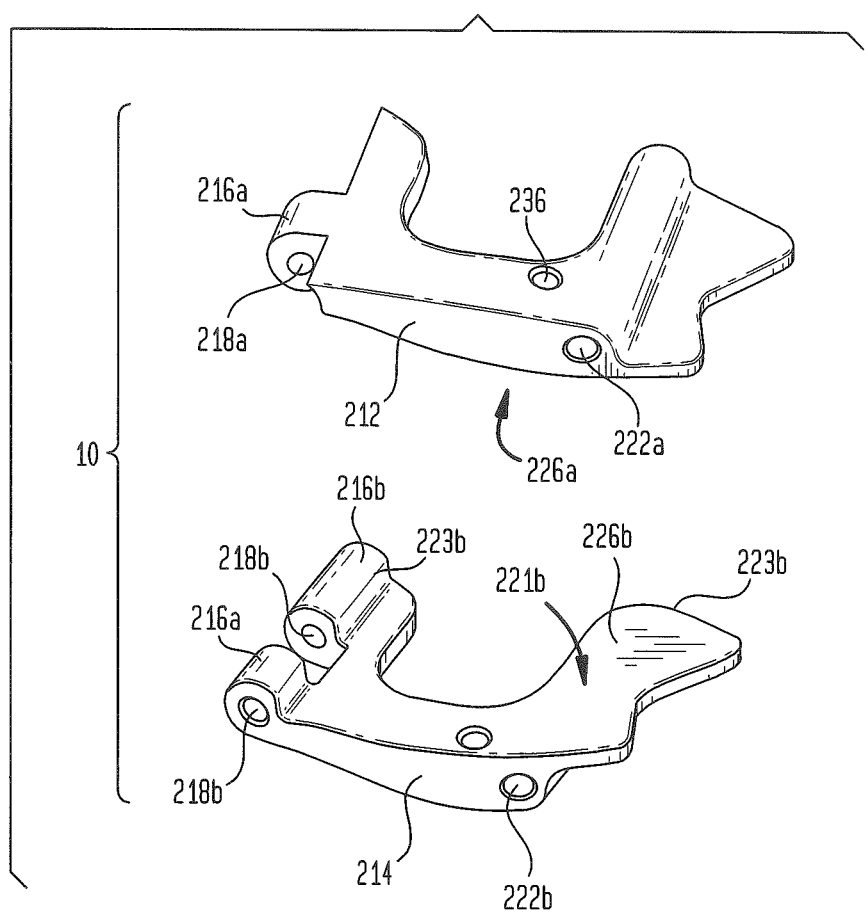
FIG. 13 is an exploded view of the guide shown in FIG. 12.

An alternative embodiment guide 210 is shown in FIGS. 12 and 13. Guide 210 includes a first arm 212 and a second arm 214 which are connected using a pin 250 that is inserted through hole 218a, included in first arm 212, and hole 218b, included in second arm 214. Preferably, hole 218a and hole 218b are located in respective hinge sections 216a, 216b of first and second arms 212, 214 which interdigitate when first and second arms 212, 214 are assembled together. First and second arms 212, 214 each include a cutout portion 221a, 221b, which are positioned so as to substantially align with each other when guide 210 is assembled, and which allow cutting guide 210 to be positioned so as to straddle the patellar tendon of the patient as shown in FIG. 12. This straddling of the patellar tendon allows the back edge sections 223a, 223b of the assembled guide 210 to contact the proximal tibia on both sides of the patellar tendon.

Both first arm 212 and second arm 214 include a respective cutting guide surface 226a, 226b which can be aligned substantially parallel to one another and spaced apart from one another at a predetermined distance to form a cutting guide slot 224, which is preferably sized so as to provide support for a cutting instrument used in connection therewith. First arm 212 includes a screw hole 236 into which a screw 234 may be inserted. Screw hole 236 is positioned such that when screw 234 is advanced thereinto, it contacts cutting guide surface 226b formed in Second arm 214 and creates a force between first arm 212 and second arm 214 that causes first and second arms 212, 214 to rotate away from each other.

Figure 14:
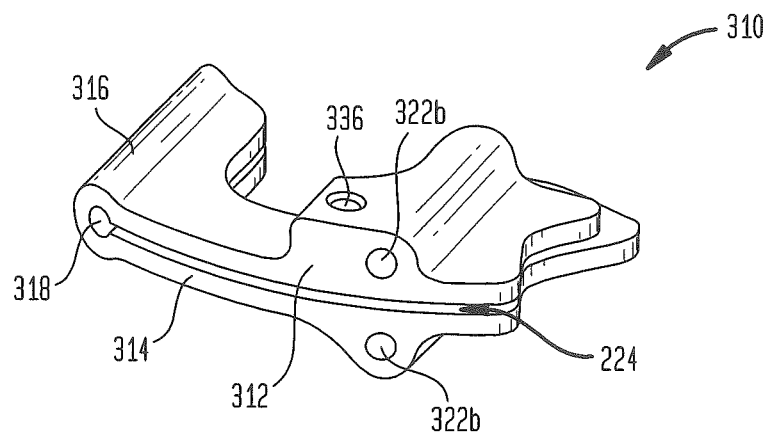
FIG. 14 is an isometric view of a further alternative embodiment of a cutting guide for use in a bone osteotomy procedure.
Figure 15:
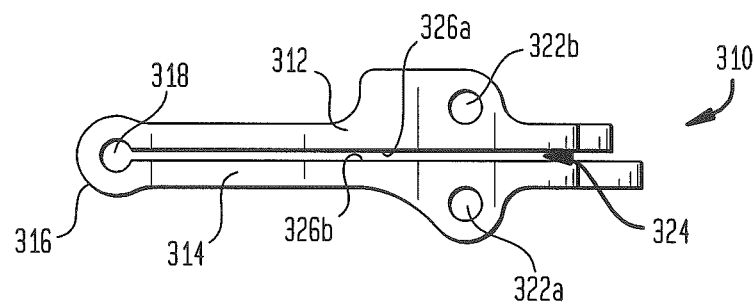
FIG. 15 is a front elevation view of the guide shown in FIG. 14.

An alternative embodiment of guide 310 is shown in FIGS. 14 and 15. This embodiment is similar in structure to guide 210, shown in FIGS. 12 and 13, but is made from a unitary piece of material, preferably plastic. First arm 312 and second arm 314 are connected by hinge portion 316, which is designed to be flexible so as to accommodate the rotation between first and second arms. The shape and thickness of the material in hinge portion 316 should be such that hinge portion 316 is more flexible than first and second arms 312, 314, and should be such that movement of first and second arms 312, 314 relative to each other can be achieved without causing breakage of guide 310 or without requiring a high level of force to be exerted on screw 334, which could cause binding of screw 334 or difficulty for the user of the device. In general the thickness of the material from which guide 310 is made should be less in hinge portion 316 than in first and second arms. Hole 318 is included in hinge portion 316 and is adapted to receive a drill bit 350 or pin therein for affixing guide 310 to the proximal tibia. Additionally, the position of hole 318 within hinge portion 316 serves to eliminate stress concentrations in hinge portion 316 during flexing thereof. Holes 322a, 322b are included in first and second arms 312, 314, respectively, and are adapted for receiving pins (not shown) therein for affixing guide 310 to the proximal tibia.

Methods for performing an opening wedge osteotomy procedure using either guide 210 or guide 310 are similar, the primary difference being that when using guide 210, first and second arms 212, 214 must be assembled together. Furthermore, the method by which both opening and closing wedge HTO procedures are conducted using guides 210 and 310 are similar to those discussed with respect to the use of guides 10 and 110, including the particular modifications that may be made to guides 210 and 310 in order to perform a closing wedge HTO procedure. The primary difference in the methods is in the formation of the cuts that is carried out in the procedure. Unlike guides 10 and 110, guides 210 and 310 do not extend along either the medial or lateral side of the proximal tibia. Accordingly, in order to extend the cuts in the proximal tibia behind the patellar tendon, a different procedure is used. Specifically, the cut is started, preferably by driving a cutting instrument, such as an oscillating saw, through the proximal tibia in a generally anterior-posterior direction, without interfering with the patellar tendon. Next, the patellar tendon is retracted away from the proximal tibia, preferably in the anterior direction, and an L shaped osteotome or other similar instrument such as an OTIS saw is placed behind and around the patellar tendon and used to finish the cut. The use of L-shaped cutting instruments in HTO procedures is discussed in co-pending U.S. patent application Ser. No. 11/480,648, which is incorporated by reference herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of performing a bone osteotomy procedure, comprising:
engaging a distraction device to a bone, the distraction device including a first arm and a second arm connected together at a hinge portion such that the first and second arms are rotatable with respect to one another about the hinge portion between a closed position and an open position, the distraction device further including a distraction mechanism operatively connected to the first and second arms so as to drive the rotation of the first and second arms with respect to one another, wherein the first arm has a first rounded groove formed therein and the second arm has a second rounded groove formed therein, such that the first and second rounded grooves together define a substantially circular bore when the first and second arms are in the closed position; and
actuating the distraction mechanism such that the first and second arms rotate with respect to one another, whereby opposing surfaces of a cut formed in the bone move with respect to one another.

2. The method of claim 1, wherein the bone is a proximal tibia, and wherein the step of engaging the distraction device to the bone includes engaging the distraction device to an anterior portion of the proximal tibia.

3. The method of claim 1, wherein the step of engaging the distraction device to the bone includes engaging the bone with a first affixation member extending laterally from the first arm and a second affixation member extending laterally from the second arm.

4. The method of claim 3, wherein the first affixation member is a first fixation pin received within a first fixation hole of the first arm, and wherein the second affixation member is a second fixation pin received within a second fixation hole of the second arm.

5. The method of claim 1, wherein the distraction mechanism includes a screw adapted to drive the rotation of the first and second arms with respect to one another upon rotation of the screw.

6. The method of claim 1, further comprising the step of forming the cut in the bone before the step of actuating the distraction mechanism.

7. The method of claim 6, wherein the step of forming the cut in the bone includes guiding a cutting instrument along a first cutting guide surface on the first arm and a second cutting guide surface on the second arm.

8. The method of claim 1, wherein the step of actuating the distraction mechanism causes the first and second arms to rotate away from one another towards the open position, whereby the opposing surfaces of the cut move away from one another towards a distracted position.

9. The method of claim 8, further comprising forming a cylindrical void in the bone before the step of actuating the distraction mechanism, wherein a first semi-cylindrical portion of the void is defined on a first side of the cut and a second semi-cylindrical portion of the void is defined on an opposing second side of the cut.

10. The method of claim 9, further comprising inserting a spacer into the cut after the step of actuating the distraction mechanism, the spacer having a first semi-cylindrical projection and a second semi-cylindrical projection on opposing sides thereof, wherein the step of inserting the spacer into the cut comprises mating the first semi-cylindrical projection with the first semi-cylindrical portion of the void and mating the second semi-cylindrical projection with the second semi-cylindrical portion of the void.

11. The method of claim 10, wherein the opposing surfaces of the cut comprise a first surface and an opposing second surface, wherein the spacer has a first angled surface and an opposing second angled surface, and wherein, after the step of inserting the spacer into the cut, the first angled surface of the spacer abuts the first surface of the cut and the second angled surface of the spacer abuts the second surface of the cut, the first and second angled surfaces being angled with respect to one another so as to substantially match an angle defined between the first and second surfaces of the cut in the distracted position.

12. The method of claim 9, wherein the step of forming the cylindrical void in the bone includes guiding a drill along the substantially circular bore defined by the first and second rounded grooves in the respective first and second arms when the first and second arms are in the closed position.

13. The method of claim 1, wherein the distraction device includes a plurality of holes spaced apart along the hinge portion, each of the holes being adapted to receive a hinge pin therein, wherein a location of an axis of rotation of the first and second arms with respect to one another is defined by a position of the hinge pin when the hinge pin is selectively positioned into one of the holes.

14. A method of performing a bone osteotomy procedure, comprising:
engaging a distraction device to a bone, the distraction device including a first arm and a second arm connected together at a hinge portion such that the first and second arms are rotatable with respect to one another about the hinge portion between a closed position and an open position, the distraction device further including a distraction mechanism operatively connected to the first and second arms so as to drive the rotation of the first and second arms with respect to one another, wherein the hinge portion includes a plurality of holes spaced apart therealong, each of the holes being adapted to receive a hinge pin therein, wherein a location of an axis of rotation of the first and second arms with respect to one another is defined by a position of the hinge pin when the hinge pin is selectively positioned into one of the holes; and
actuating the distraction mechanism such that the first and second arms rotate with respect to one another, whereby opposing surfaces of a cut formed in the bone move with respect to one another.

15. The method of claim 14, wherein the bone is a proximal tibia, and wherein the step of engaging the distraction device to the bone includes engaging the distraction device to an anterior portion of the proximal tibia.

16. The method of claim 14, wherein the step of engaging the distraction device to the bone includes engaging the bone with a first affixation member extending laterally from the first arm and a second affixation member extending laterally from the second arm.

17. The method of claim 16, wherein the first affixation member is a first fixation pin received within a first fixation hole of the first arm, and wherein the second affixation member is a second fixation pin received within a second fixation hole of the second arm.

18. The method of claim 14, wherein the distraction mechanism includes a screw adapted to drive the rotation of the first and second arms with respect to one another upon rotation of the screw.

19. The method of claim 14, further comprising the step of forming the cut in the bone before the step of actuating the distraction mechanism.

20. The method of claim 19, wherein the step of forming the cut in the bone includes guiding a cutting instrument along a first cutting guide surface on the first arm and a second cutting guide surface on the second arm.

21. The method of claim 14, wherein the step of actuating the distraction mechanism causes the first and second arms to rotate away from one another towards the open position, whereby the opposing surfaces of the cut move away from one another towards a distracted position.

\* \* \* \* \*